United States Patent

Matsuda

(10) Patent No.: US 8,989,459 B2
(45) Date of Patent: Mar. 24, 2015

(54) IMAGE PROCESSING APPARATUS, IMAGE PROCESSING PROGRAM PRODUCT, AND IMAGE PROCESSING METHOD

(75) Inventor: Takehiro Matsuda, Hachioji (JP)

(73) Assignee: Olympus Corporation, Tokyo (JP)

( * ) Notice: Subject to any disclaimer, the term of this patent is extended or adjusted under 35 U.S.C. 154(b) by 715 days.

(21) Appl. No.: 12/637,162

(22) Filed: Dec. 14, 2009

(65) Prior Publication Data
US 2010/0092055 A1 Apr. 15, 2010

Related U.S. Application Data

(63) Continuation of application No. PCT/JP2008/059997, filed on May 30, 2008.

(30) Foreign Application Priority Data

Jun. 14, 2007 (JP) ................................. 2007-158027

(51) Int. Cl.
*G06K 9/00* (2006.01)
*G06T 7/00* (2006.01)
(Continued)

(52) U.S. Cl.
CPC .......... *G06T 7/0012* (2013.01); *A61B 1/00009* (2013.01); *A61B 1/041* (2013.01); *G06T 2207/10068* (2013.01); *G06T 2207/30028* (2013.01); *G06T 2207/30092* (2013.01); *G06T 2207/30096* (2013.01); *G06T 7/0081* (2013.01); *G06T 2207/20141* (2013.01)
USPC ....................................................... 382/128

(58) Field of Classification Search
CPC ................................ H04N 5/32; G06T 7/0012
USPC .............................................. 382/128; 378/19
See application file for complete search history.

(56) References Cited

U.S. PATENT DOCUMENTS 5,057,682 A * 10/1991 Michon et al. ............. 250/214 C
5,349,951 A * 9/1994 Ito et al. ........................ 600/310
5,694,933 A * 12/1997 Madden et al. ............... 600/431
(Continued)

FOREIGN PATENT DOCUMENTS

EP 1 875 855 A1 1/2008
JP 2002-165757 6/2002
(Continued)

OTHER PUBLICATIONS

Machine translation of JP 2004016721 retrieved from http://www4.ipdl.inpit.go.jp/Tokujitu/PAJdetail.ipdl?N0000=60&N0120=01&N2001=2&N3001=2004-016721 on Jul. 19, 2012, 14 total pages.*
(Continued)

*Primary Examiner* — Matthew Bella
*Assistant Examiner* — Dennis Rosario
(74) *Attorney, Agent, or Firm* — Scully, Scott, Murphy & Presser, PC

(57) ABSTRACT

An image processing apparatus includes a suspected-lesion-region extracting unit that extracts a suspected lesion region from an in-vivo image that is obtained by taking an image of inside of body; a groove determining unit that determines whether the suspected lesion region is a region corresponding to a shadow of a groove that is formed between in-vivo organ walls; and a lesion-region extracting unit that extracts a lesion region using the suspected lesion region and a result of determination by the groove determining unit.

35 Claims, 10 Drawing Sheets

(51) Int. Cl.
*A61B 1/00* (2006.01)
*A61B 1/04* (2006.01)

(56) References Cited

U.S. PATENT DOCUMENTS

| | | | |
|---|---|---|---|
| 6,937,776 B2 * | 8/2005 | Li et al. | 382/260 |
| 7,245,754 B2 * | 7/2007 | Goto | 382/128 |
| 7,272,250 B2 * | 9/2007 | Schneider et al. | 382/128 |
| 7,298,878 B2 * | 11/2007 | Goto | 382/128 |
| 7,355,597 B2 * | 4/2008 | Laidlaw et al. | 345/419 |
| 7,483,023 B2 * | 1/2009 | Cardenas et al. | 345/419 |
| 7,689,016 B2 * | 3/2010 | Stoecker et al. | 382/128 |
| 7,953,261 B2 * | 5/2011 | Nishimura et al. | 382/128 |
| 8,090,431 B2 * | 1/2012 | Wang et al. | 600/473 |
| 8,111,896 B2 * | 2/2012 | Agliozzo et al. | 382/132 |
| 8,600,125 B2 * | 12/2013 | Kaufman et al. | 382/128 |
| 2005/0207630 A1 * | 9/2005 | Chan et al. | 382/131 |

FOREIGN PATENT DOCUMENTS

| | | |
|---|---|---|
| JP | 2004016721 A * | 1/2004 |
| JP | 2004-521693 | 7/2004 |
| JP | 2006-304995 | 11/2006 |
| WO | WO 02/073507 A2 | 9/2002 |
| WO | WO 2006/117932 A1 | 11/2006 |

OTHER PUBLICATIONS

Yokomise et al., Importance of Intrapulmonary Lymph Nodes in the Differential Diagnosis of Small Pulmonary Nodular Shadows, Mar. 1998, CHEST, vol. 113, No. 3, pp. 703-706.*

International Search Report dated Aug. 26, 2008.

Tjoa, M.P., et al., "Segmentation of Clinical Endoscopic Image Based on Homogeneity and Hue", Proceedings of the 23$^{rd}$ Annual International Conference of the IEEE Engineering in Medicine and Biology Society vol. 3, Oct. 25-28, 2001; pp. 2665-2668.

European Supplementary Search Report dated Apr. 12, 2012 from corresponding European Patent Application No. EP 08 76 4915.8.

* cited by examiner

FIG.7-1

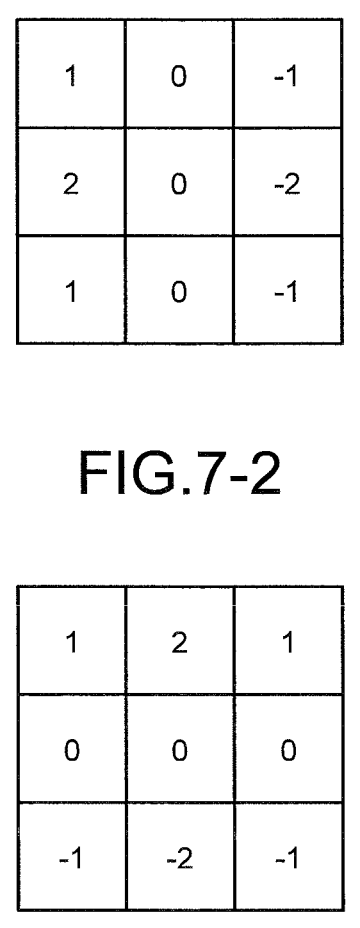

| 1 | 0 | -1 |
|---|---|----|
| 2 | 0 | -2 |
| 1 | 0 | -1 |

FIG.7-2

| 1 | 2 | 1 |
|---|---|---|
| 0 | 0 | 0 |
| -1 | -2 | -1 |

IMAGE PROCESSING APPARATUS, IMAGE PROCESSING PROGRAM PRODUCT, AND IMAGE PROCESSING METHOD

CROSS-REFERENCE TO RELATED APPLICATIONS

This application is a continuation of PCT international application Ser. No. PCT/JP2008/059997 filed on May 30, 2008 which designates the United States, incorporated herein by reference, and which claims the benefit of priority from Japanese Patent Application No. 2007-158027, filed on Jun. 14, 2007, incorporated herein by reference.

BACKGROUND OF THE INVENTION

1. Field of the Invention

The present invention relates to an image processing apparatus, an image processing program, and an image processing method that process an in-vivo image that is obtained by taking an image of inside of body cavity.

2. Description of the Related Art

In recent years, swallow-type capsule endoscopes have been proposed in the field of endoscopy. The capsule endoscope has various functions, such as imaging, wireless communication, and illuminating sites to be imaged. The capsule endoscope is swallowed by a patient through the mouth and then introduced inside the body. Then, while moving inside the body cavity along, for example, the gullet, the stomach, and the small intestine by peristaltic action, the capsule endoscope sequentially takes in-vivo images and wirelessly sends the taken in-vivo images to a receiving device, which is arranged outside the body, until the capsule endoscope is naturally excreted outside the body.

The capsule endoscope takes a large number of in-vivo images during the period from when it is swallowed by the patient through the mouth to when it is naturally excreted. Therefore, image processing apparatuses that detect a lesion from the taken in-vivo images by image processing are used. A typical image processing apparatus that detects a lesion using the in-vivo images splits an image of inside of the alimentary truck into blocks, calculates color data for each block, and compares the color data of a region well-known for lesions, such as a bleeding region, with a reference value representing color data of healthy tissues (see Japanese Patent Application Laid-open No. 2004-521693).

SUMMARY OF THE INVENTION

An image processing apparatus according to an aspect of the present invention includes a suspected-lesion-region extracting unit that extracts a suspected lesion region from an in-vivo image that is obtained by taking an image of inside of body; a groove determining unit that determines whether the suspected lesion region is a region corresponding to a shadow of a groove that is formed between in-vivo organ walls; and a lesion-region extracting unit that extracts a lesion region using the suspected lesion region and a result of determination by the groove determining unit.

An image processing program product according to another aspect of the present invention has a computer readable medium including programmed instructions that, when executed by a computer, causes the computer to perform a suspected-lesion-region extracting that extracts a suspected lesion region from an in-vivo image that is obtained by taking an image of inside of body; a groove determining that determines whether the suspected lesion region is a region corresponding to a shadow of a groove that is formed between in-vivo organ walls; and a lesion-region extracting that extracts a lesion region using the suspected lesion region and a result of determination by the groove determining.

An image processing method according to still another aspect of the invention includes a suspected-lesion-region extracting that extracts a suspected lesion region from an in-vivo image that is obtained by taking an image of inside of body; a groove determining that determines whether the suspected lesion region is a region corresponding to a shadow of a groove that is formed between in-vivo organ walls; and a lesion-region extracting that extracts a lesion region using the suspected lesion region and a result of determination by the groove determining.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7-1 is a schematic diagram showing a horizontal sobel filter;

FIG. 7-2 is a schematic diagram showing a vertical sobel filter;

FIG. 9-1 is a schematic diagram that explains how to define a surrounding pixel area;

FIG. 9-2 is a schematic diagram that explains how to define the surrounding pixel area;

DETAILED DESCRIPTION OF THE PREFERRED EMBODIMENTS

Exemplary embodiments of image processing apparatuses, image processing programs, and image processing methods according to the present invention are described in detail below with reference to the accompanying drawings.

Figure 1:
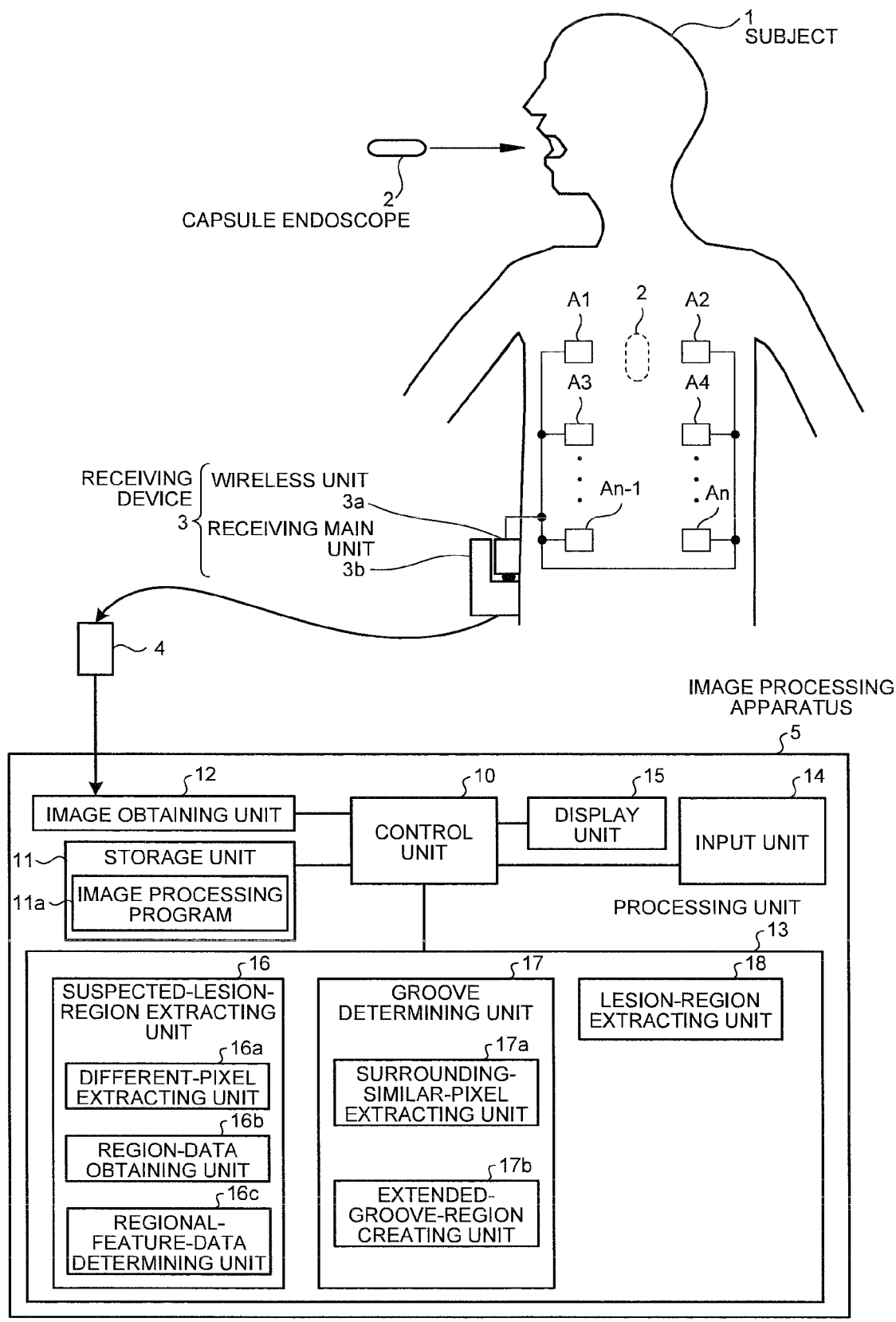
FIG. 1 is a schematic diagram showing a whole configuration of an image processing system that includes an image processing apparatus.

FIG. 1 is a schematic diagram showing a whole configuration of an image processing system that includes an image processing apparatus according to an embodiment of the present invention. As shown in FIG. 1, the image processing system includes a capsule endoscope 2 that takes in-vivo images of inside of body cavity of a subject 1; a receiving device 3 that receives the in-vivo images wirelessly from the capsule endoscope 2; and an image processing apparatus 5 that processes the in-vivo images that are taken by the capsule endoscope 2 using the in-vivo images that are received by the receiving device 3. For example, a recording medium that can be carried (portable recording medium) 4 is used for input/output of data on the in-vivo images between the receiving device 3 and the image processing apparatus 5.

The receiving device 3 includes a wireless unit 3a that receives wireless signals from the capsule endoscope 2 via a group of receiving antennas A1 to An that is attached to an outer surface of the subject 1; and a receiving main unit 3b that processes the wireless signals received from the wireless unit 3a. The wireless unit 3a and the receiving main unit 3b are connected to each other via a connector or the like in a detachable manner. The receiving device 3 is designed such that the portable recording medium 4 is attached to and detached from it. The receiving device 3 receives image data on the in-vivo images of inside of the subject 1 that are taken by the capsule endoscope 2 and sequentially stores the data in the portable recording medium 4.

The image processing apparatus 5 includes a control unit 10 that controls the whole image processing apparatus 5; a storage unit 11; an image obtaining unit 12, to which the portable recording medium 4 is detachably attached and which obtains the in-vivo images from the portable recording medium 4; a processing unit 13 that performs predetermined image processing on the in-vivo images that are obtained by the image obtaining unit 12; an input unit 14 that inputs various instruction data; and a display unit 15 that displays a result of the image processing performed by the processing unit 13, etc.

The storage unit 11 includes, for example, a data recording medium and a reading device that reads data therefrom. The data recording medium is, for example, various IC memories, such as a rewritable flash memory including ROM and RAM, a built-in hard disk, a hard disk that is connected via a data communications terminal, and a CD-ROM. Programs related to operation of the image processing apparatus 5, programs that implement various functions of the image processing apparatus 5, and data that is used to run these programs, etc., are stored in the storage unit 11. Moreover, an image processing program 11a with which the processing unit 13 processes the in-vivo images and extracts a lesion region is stored in the storage unit 11.

The processing unit 13 includes a suspected-lesion-region extracting unit 16 that extracts a suspected convexity lesion region and a suspected concavity lesion region using a pixel having a pixel value that is different from those of the surrounding pixels; a groove determining unit 17 that determines whether the suspected concavity lesion region is a region corresponding to a shadow of a groove that is formed between organ walls in the body cavity (hereinafter, "groove region"); and a lesion-region extracting unit 18 that excludes the suspected concavity lesion region that is determined to be the groove region, thereby extracting a lesion region.

The suspected-lesion-region extracting unit 16 includes a different-pixel extracting unit 16a that extracts a pixel having a pixel value different from those of the surrounding pixels; a region-data obtaining unit 16b that extracts a region that is possibly a suspected lesion region using the extracted pixel and calculates feature data of the extracted region; and a regional-feature-data determining unit 16c that extracts the suspected lesion region, i.e., the suspected convexity lesion region and the suspected concavity lesion region from the regions that are possibly the suspected lesion regions using the calculated feature data.

The groove determining unit 17 includes a surrounding-similar-pixel extracting unit 17a that extracts a pixel having a pixel value close to those of pixels that form the suspected concavity lesion region from an area surrounding the suspected convexity lesion region; and an extended-groove-region creating unit 17b that creates an extended groove region surrounding the suspected concavity lesion region using the pixels of the suspected concavity lesion region and the pixel extracted from the area surrounding the suspected concavity lesion region and determines, using a shape feature-data variation amount between the suspected concavity lesion region and the extended groove region that is created from the suspected concavity lesion region, whether the suspected concavity lesion region is the groove region.

Figure 2:
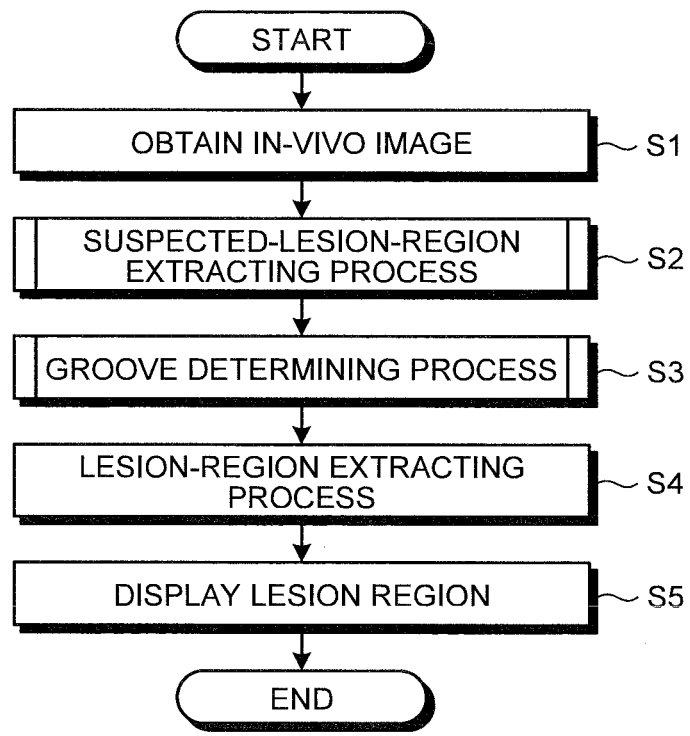
FIG. 2 is a whole flowchart showing a process performed by the image processing apparatus.

A lesion-region extracting process performed by the image processing apparatus 5 according to the present embodiment is described below. FIG. 2 is a whole flowchart showing the process performed by the image processing apparatus 5. The process described below is implemented when the units of the image processing apparatus 5 operate in accordance with the image processing program 11a that is stored in the storage unit 11.

As shown in FIG. 2, the image obtaining unit 12 first reads image data on an in-vivo image from the attached portable recording medium 4 and obtains the in-vivo image that is taken by the capsule endoscope 2 (Step S1). Then, the suspected-lesion-region extracting unit 16 of the processing unit 13 performs a suspected-lesion-region extracting process, i.e., extracts a suspected concavity lesion region and a suspected convexity lesion region from the in-vivo image that is obtained at Step S1 as suspected lesion regions (Step S2). The groove determining unit 17 performs a groove determining process, i.e., determines whether the suspected concavity lesion region is the groove region (Step S3). The lesion-region extracting unit 18 performs a lesion-region extracting process, i.e., extracts the lesion region from the suspected concavity lesion regions and the suspected convexity lesion regions using a result of the determination by the groove determining process (Step S4). The processing unit 13 then displays the lesion region that is extracted at Step S4 on the display unit 15 via the control unit 10 (Step S5), and the process performed by the image processing apparatus 5 ends.

Figure 3:
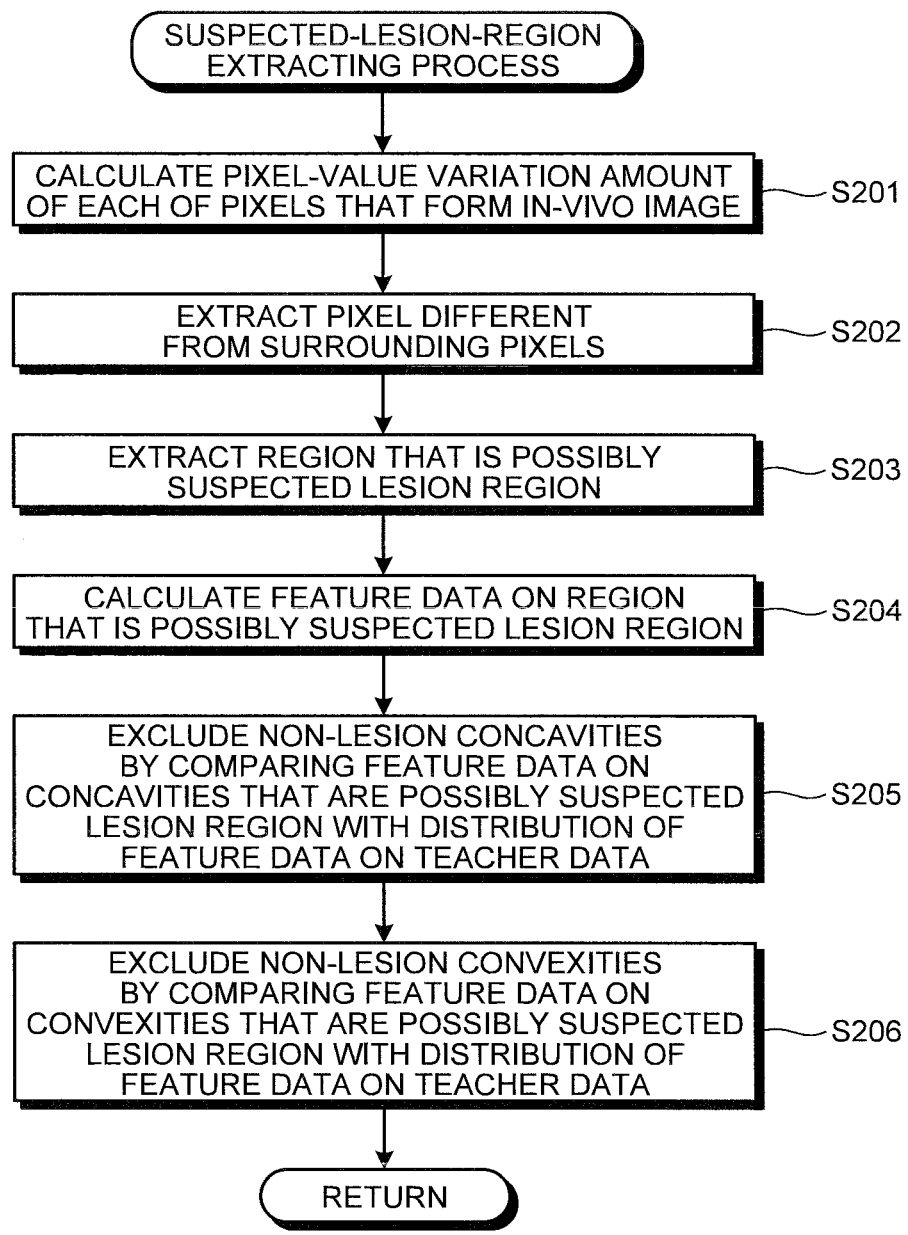
FIG. 3 is a flowchart showing a suspected-lesion-region extracting process in detail.

The suspected-lesion-region extracting process at Step S2 of FIG. 2 is described below. FIG. 3 is a flowchart showing the suspected-lesion-region extracting process in detail. The suspected lesion region is considered to be a section having a pixel value different from those of the surrounding pixels that form healthy tissues. In the suspected-lesion-region extracting process, the different-pixel extracting unit 16a sets the pixels that form the in-vivo image to a focus pixel sequentially and calculates a pixel-value variation amount using the focus pixel and surrounding pixels that are away from the focus pixel by a predetermine number of pixels λ or a distance equivalent to the number of pixels λ (Step S201). The color component corresponding to a blood absorbing band is used to calculate the pixel-value variation amount. If the in-vivo image is an RGB image, a change of the pixel value due to a lesion tends to appear in the G component corresponding to the blood absorbing band. Therefore, in the present embodiment, the RGB image is used and the G component image out of the RGB image is used to calculate the pixel-value variation amount.

Figure 4:
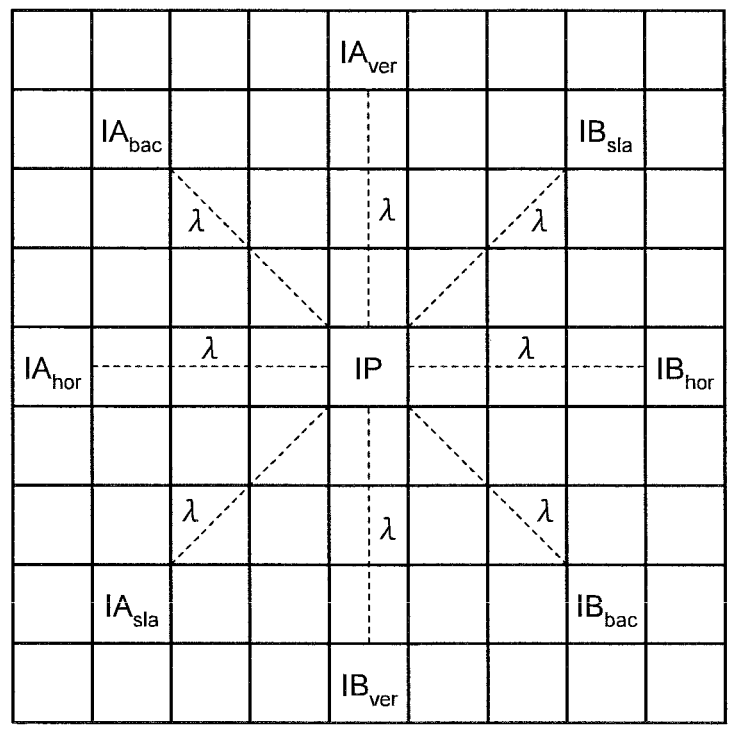
FIG. 4 is a schematic diagram that explains a pixel-value-variation-amount calculating method.

FIG. 4 is a schematic diagram that explains a pixel-value-variation-amount calculating method. In the calculation of the pixel-value variation amount, for example, four directions with respect to a focus pixel IP are used including the horizontal direction, the vertical direction, the lower-left-andupper-right direction, and the upper-left-and-lower-right direction. As shown in FIG. 4, pixels away from the focus pixel IP in the horizontal direction by the predetermined number of pixels λ or the distance equivalent to the number of pixels λ are assumed to be surrounding pixels $IA_{hor}$ and $IB_{hor}$; pixels away from the focus pixel IP in the vertical direction are assumed to be surrounding pixels $IA_{ver}$ and $IB_{ver}$; pixels away from the focus pixel IP in the lower-left-and-upper-right direction are assumed to be surrounding pixels $IA_{sla}$ and $IB_{sla}$; pixels away from the focus pixel IP in the upper-left-and-lower-right direction are assumed to be surrounding pixels $IA_{bac}$ and $IB_{bac}$. The pixel-value variation amount is calculated using the focus pixel and these pixels.

A pixel-value variation amount $V_{hor}$ in the horizontal direction with respect to the focus pixel IP is calculated in accordance with the following equation (1) using the focus pixel IP, the surrounding pixels $IA_{hor}$ and $IB_{hor}$:

$$V_{hor} = IP - IM_{hor} \quad (1)$$

where $$IM_{hor} = \frac{IA_{hor} + IB_{hor}}{2}$$

A pixel-value variation amount $V_{ver}$ in the vertical direction with respect to the focus pixel IP is calculated in accordance with the following equation (2) using the focus pixel IP, the surrounding pixels $IA_{ver}$ and $IB_{ver}$:

$$V_{ver} = IP - IM_{ver} \quad (2)$$

where $$IM_{ver} = \frac{IA_{ver} + IB_{ver}}{2}$$

A pixel-value variation amount $V_{sla}$ in the lower-left-and-upper-right direction with respect to the focus pixel IP is calculated in accordance with the following equation (3) using the focus pixel IP, the surrounding pixels $IA_{sla}$ and $IB_{sla}$:

$$V_{sla} = IP - IM_{sla} \quad (3)$$

where $$IM_{sla} = \frac{IA_{sla} + IB_{sla}}{2}$$

A pixel-value variation amount $V_{bac}$ in the upper-left-and-lower-right direction with respect to the focus pixel IP is calculated in accordance with the following equation (4) using the focus pixel IP, the surrounding pixels $IA_{bac}$ and $IB_{bac}$:

$$V_{bac} = IP - IM_{bac} \quad (4)$$

where $$IM_{bac} = \frac{IA_{bac} + IB_{bac}}{2}$$

The pixel-value variation amounts $V_{hor}$, $V_{ver}$, $V_{sla}$, and $V_{bac}$ that are calculated in accordance with equations (1) to (4) are collectively referred to as pixel-value variation amount $V_{dir}$. The suffix dir indicates any of the predetermined directions with respect to the focus pixel IP (any of the vertical direction, the horizontal direction, the lower-left-and-upper-right direction, and the upper-left-and-lower-right direction in the present embodiment).

If a region of the focus pixel IP is protruding more than the surroundings, the pixel-value variation amount $V_{dir}$ is a positive value. In contrast, if a region of the focus pixel IP is depressing more than the surroundings, the pixel-value variation amount $V_{dir}$ is a negative value. This is because, in general, a region protruding more than the surroundings is brighter than the surroundings and has a higher brightness value, while a region depressing more than the surroundings is darker than the surroundings and has a lower brightness value.

Subsequently, as shown in FIG. 3, the different-pixel extracting unit 16a extracts a pixel having a pixel value meaningfully different from those of the surrounding pixels as a pixel associated with a suspected lesion using the calculated pixel-value variation amount $V_{dir}$ (Step S202). At that step, the different-pixel extracting unit 16a determines convexity and concavity in an area of each of the pixels that form the in-vivo image and extracts a pixel that is determined as the suspected convexity lesion region or a pixel that is determined as the suspected concavity lesion region. Specifically, if it is determined using the calculated pixel-value variation amount of each direction that a pixel has the pixel-value variation amount in every direction larger than a predetermined convexity threshold (ConvexityTh), i.e., the pixel satisfies $V_{hor}$>ConvexityTh, $V_{ver}$>ConvexityTh, $V_{sla}$>ConvexityTh, and $V_{bac}$>ConvexityTh, the different-pixel extracting unit 16a determines that the pixel is protruding more than the surroundings and extracts the pixel. In contrast, if it is determined using the calculated pixel-value variation amount of each direction that a pixel has the pixel-value variation amount in every direction smaller than a predetermined concavity threshold (ConcaveTh), i.e., the pixel satisfies $V_{hor}$>ConcaveTh, $V_{ver}$>ConcaveTh, $V_{sla}$>ConcaveTh, and $V_{bac}$>ConcaveTh, the different-pixel extracting unit 16a determines that the pixel is depressing more than the surroundings and extracts the pixel.

Subsequently, the region-data obtaining unit 16b defines a region of the suspected convexity or concavity lesion that is extracted at Step S202 and extracts a region that is possibly the suspected lesion region (Step S203). Specifically, the region-data obtaining unit 16b first creates a convexity binary image, in which the pixel that is protruding more than the surroundings is "1" and the pixel that is no protruding more than the surroundings is "0", and a concavity binary image, in which the pixel that is depressing more than the surroundings is "1" and the pixel that is no depressing more than the surroundings is "0". The region-data obtaining unit 16b then performs the well-known labeling process on each of the convexity binary image and the concavity binary image and assigns a unique value (label) to connection components (a group of pixels connected to each other) of the binary images, thereby defining the region. By this definition, a convexity image containing labeled convexities that are obtained by defining the convexities in the convexity binary image and a concavity image containing labeled concavities that are obtained by defining the concavities in the concavity binary image are obtained. The region-data obtaining unit 16b then determines the convexity to be the convexity that is possibly the suspected lesion region and the concavity to be the concavity that is possibly the suspected lesion region and determines both the convexity and the concavity to be the regions that is possibly the suspected lesion regions.

Subsequently, the region-data obtaining unit 16b calculates feature data on each of the regions that are possibly the suspected lesion regions that are extracted at Step S203 (Step S204). The feature data is expressed by, for example, the average of pixel values within the region ($R_{abs\_m}$, $G_{abs\_m}$, $B_{abs\_m}$), the average of pixel-value variation amounts within the region ($R_{var\_m}$, $G_{var\_m}$, $B_{var\_m}$), the area of the region $S\_m$, the perimeter of the region $L\_m$, the Feret's diameter of the region $Fere\_m(\theta)$, the longer diameter of the region $L_{l\_m}$, the shorter diameter of the region $L_{s\_m}$, the ratio between the longer diameter and the shorter diameter $L_{r\_m}$, the edge strength of the outline of the region $E\_m$, and the degree of circularity of the region $C\_m$. These values are calculated from each of the regions that are possibly the suspected lesion regions. The suffix m indicates an identification number of the suspected lesion region.

The average of pixel values within the region ($R_{abs\_m}$, $G_{abs\_m}$, $B_{abs\_m}$) is obtained by calculating a sum of R values, a sum of G values, and a sum of B values of the pixels that are in the same suspected lesion region and then dividing the sums by the area of the region.

To calculate the average of pixel-value variation amounts within the region ($R_{var\_m}$, $G_{var\_m}$), it is necessary to calculate the pixel-value variation amount of each of R, G, and B components of each of the pixels that form the in-vivo image. The pixel-value variation amount $V_{dir}$ that is calculated at Step S201 can be used as the pixel-value variation amount of the G component.

When it is focused on the G component, as for the pixels that are other than the background of the convexity image or the concavity image (labeled pixels), an average of the directional pixel-value variation amounts $V_r$ is calculated using the following equation (5). As for the pixels that are the background of the convexity image or the concavity image (unlabeled pixels, i.e., pixels that are neither the convexity nor the concavity), $V_r=0$.

$$V_r = \frac{V_{hor} + V_{ver} + V_{sla} + V_{bac}}{4} \quad (5)$$

The averages of the directional pixel-value variation amounts $V_r$ in the G component of all the pixels in the same suspected lesion region are added, and the calculated sum is divided by the area of the region, whereby the average of the pixel-value variation amounts within the region $G_{var\_m}$ is calculated. Alternatively, the average of the pixel-value variation amounts within the region can be calculated using the maximum value or the minimum value of the pixel-value variation amounts $V_{dir}$ instead of the average of the directional pixel-value variation amounts.

As for the R component and the B component, the pixel-value variation amount of each direction is calculated using equations (1) to (4) in the same manner as described with reference to FIG. 4. The average of the directional pixel-value variation amounts $V_r$ is then calculated in the same manner as in the G component. The averages of the directional pixel-value variation amounts of all the pixels in the same suspected lesion region are added and the calculated sum is divided by the area of the region, whereby the averages of the pixel-value variation amounts within the region $R_{var\_m}$ and $B_{var\_m}$ are calculated. It is allowable to calculate the average of the direction pixel-value variation amounts $V_r$ in the R component and the B component only if the pixel is extracted as the convexity or the concavity using the average of the direction pixel-value variation amounts $V_r$ in the G component, i.e., the pixel has the pixel value "1" in the convexity binary image or the concavity binary image. This reduces the calculation load, which makes high-speed processing possible.

The area of the region $S\_m$ is calculated on each suspected lesion region by counting the number of pixels that are in the same suspected lesion region.

Figure 5:
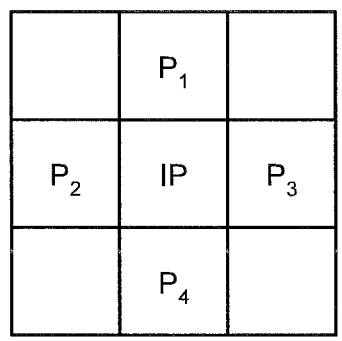
FIG. 5 is a schematic diagram that explains how to determine an outline pixel.

The perimeter of the region $L\_m$ is calculated on each suspected lesion region by counting the number of pixels that are positioned on the outline of the region from among the pixels that are in the same suspected lesion region. Specifically, a pixel from among the pixels that form the in-vivo image is assumed to be a focus pixel and whether the focus pixel is an outline pixel is determined. The pixels that form the in-vivo image are set to the focus pixel sequentially. FIG. 5 is a schematic diagram that explains how to determine the outline pixel. As shown in FIG. 5, four pixels $P_1$ to $P_4$ that are adjacent to the focus pixel IP are assumed to be the surrounding pixels. It is then determined whether any of the surrounding pixels $P_1$ to $P_4$ is a background pixel or a pixel with a label number different from that of the focus pixel IP. If the determination is positive, the focus pixel IP is determined to be an outline pixel. The number of the outline pixels that are determined in this manner is counted on each suspected lesion region.

Figure 6:
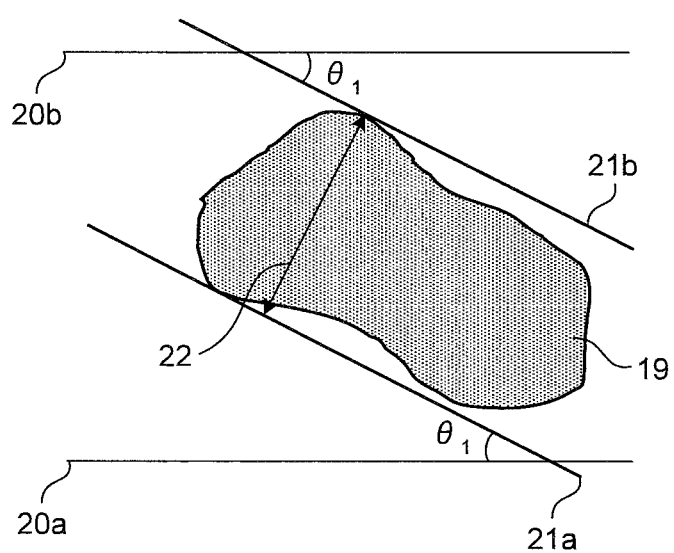
FIG. 6 is a schematic diagram that explains how to calculate a Feret's diameter $Fere\_m(\theta_1)$.

The Feret's diameter of the region $Fere\_m(\theta_1)$, the longer diameter of the region $L_{l\_m}$, and the shorter diameter of the region $L_{s\_m}$ are calculated in the following procedure. FIG. 6 is a schematic diagram that explains how to calculate the Feret's diameter $Fere\_m(\theta_1)$ of a suspected lesion region 19. As shown in FIG. 6, two lines 21a and 21b tangent to the suspected lesion region 19 are obtained in such a manner that an angle between the tangent line 21a and a horizontal line 20a and an angle between the tangent line 21b and a horizontal line 20b are set to $\theta_1$ and the distance between the tangent lines 21a and 21b are set as long as possible. A distance 22 between the two tangent lines is the Feret's diameter $Fere\_m(\theta_1)$ of the suspected lesion region 19 at the angle $\theta_1$. The Feret's diameter of the target suspected lesion region is calculated at each angle $\phi$. The maximum Feret's diameter of the calculated Feret's diameters is the longer diameter of the region $L_{l\_m}$. The minimum Feret's diameter of the calculated Feret's diameters is the shorter diameter of the region $L_{s\_m}$.

The Feret's diameter $Fere\_m(0)$ where the angle $\theta_1$ is 0 degree and the Feret's diameter $Fere\_m(90)$ where the angle $\theta_1$ is 90 degrees are calculated using the following equations (6) and (7) using the start coordinate point ($x_S$, $y_S$) and the end coordinate point ($x_E$, $y_E$) of the bounding rectangle of the target suspected lesion region:

$$Fere\_m(0) = x_E - x_S \quad (6)$$

$$Fere\_m(90) = y_E - y_S \quad (7)$$

To calculate the Feret's diameter $Fere\_m(\phi_1)$ where the angle $\phi_1$ is other than 0 degree or 90 degrees, a y coordinate of an intersection of a line having the angle $\phi_1$ with the y axis (line of pixels with x=0), i.e., a value of an intercept $b_{\phi1}(j)$ is first calculated using the outline pixels of the target suspected lesion region. The value of the intercept $b_{\phi1}(j)$ is calculated using the following equation (8) where ($x_j$, $y_j$) is the position of the j-th outline pixel of the target suspected lesion region. The pixel position ($x_j$, $y_j$) of the outline pixel is used in equation (8). This is because every tangent line of the region is tangent to a pixel that is positioned on the outline of the region. Therefore, the Feret's diameter is calculated using only the outline pixels, i.e., part of the entire pixels in the region.

$$b_{\phi1}(j) = -\tan\phi_1 \cdot x_j - y_j \quad (8)$$

The minimum value $\text{Min\_b}_{\phi 1}$ and the maximum value $\text{Max\_b}_{\phi 1}$ of the value of the intercept, which is calculated using equation (8), of each outline pixel at the angle $\phi_1$ are then calculated using the following equations (9) and (10):

$$\text{Min\_}b_{\phi 1}=\min(b_{\phi 1}(j)) \quad (9)$$

(j=0, 1, 2, . . . , n)

$$\text{Max\_}b_{\phi 1}=\max(b_{\phi 1}(j)) \quad (10)$$

(j=0, 1, 2, . . . , n)
where n is the number of the outline pixels.

The Feret's diameter $\text{Fere\_}_m(\phi_1)$ at the angle $\phi_1$ is then calculated using the following equation (11):

$$\text{Fere\_}_m(\phi_1)=(\text{Max\_}b_{\phi 1}-\text{Max\_}b_{\phi 1})\times|\cos \phi_1| \quad (11)$$

The Feret's diameter $\text{Fere\_}_m(\phi_i)$ at a different angle $\phi_i$ is calculated using equations (8) to (11) in the same manner.

Then, the longer diameter $L_{l\_m}$, which is the maximum Feret's diameter of the Feret's diameters $\text{Fere\_}_m(\phi_i)$ of the target suspected lesion region that are calculated by increment of the angle $\phi_i$, and the shorter diameter $L_{s\_m}$, which is the minimum Feret's diameter, are calculated using the following equations (12) and (13). The angle $\phi$ used in equations (12) and (13) is an arbitrary angle. In an actual calculation of the longer diameter $L_{l\_m}$ and the shorter diameter $L_{s\_m}$, the angle $\phi$ increases appropriately by an interval, for example, 22.5 degrees.

$$L_{l\_m}=\max(\text{Fere\_}_m(\phi)) \quad (12)$$

$$L_{s\_m}=\min(\text{Fere\_}_m(\phi)) \quad (13)$$

The ratio between the longer diameter and the shorter diameter $L_{r\_m}$ is calculated using the following equation (14):

$$L_{r\_m} = \frac{L_{l\_m}}{L_{s\_m}} \quad (14)$$

The edge strength of the outline of the region $E\_{m}$ is calculated by applying an edge detecting filter shown in FIG. 7-1 or FIG. 7-2 to a grayscale image that represents either any of the R component, the G component, and the B component of the in-vivo image or an average of the R, the G, and the B components.

An edge strength image $E_1(i)$ that is created using a sobel (Sobel) filter, which is the first deviation, is expressed by the following equation (15) using an output $S1(i)$ that is a convolution of a sobel filter SF1 in the horizontal direction (x direction) shown in FIG. 7-1 and an output $S2(i)$ that is a convolution of a sobel filter SF2 in the vertical direction (y direction) shown in FIG. 7-2 in which i indicates the pixel position in the image:

$$E_1(i)=\sqrt{S1(i)^2+S2(i)^2} \quad (15)$$

Subsequently, values of the edge strength image at positions of the outline pixels are read on each suspected lesion region. All the edge strength values in the same suspected lesion region are added, and the calculated sum is divided by the perimeter $L\_{m}$ of the suspected lesion region using the following equation (16), whereby the edge strength of the outline of the region $E\_{m}$ is calculated.

$$E\_{m} = \frac{\sum_i E_1(i)}{L\_{m}} \quad (16)$$

The degree of circularity $C\_{m}$ is calculated using the following equation (17) using the area of the region $S\_{m}$ and the perimeter of the region $L\_{m}$:

$$C\_{m} = \frac{4\pi S\_{m}}{L^2\_{m}} \quad (17)$$

After the feature data of the suspected lesion region is calculated as described above, the regional-feature-data determining unit 16c refines suspected lesion regions by excluding concavities having feature data that indicates something other than lesions from the concavities that are possibly the suspected lesion regions (Step S205) as shown in FIG. 3. Specifically, the regional-feature-data determining unit 16c determines whether each concavity that is possibly the suspected lesion region is a lesion or a non-lesion by comparing the feature data with a distribution of feature data on teacher data. If, for example, the average of pixel values within the region ($R_{abs\_m}$, $G_{abs\_m}$, $B_{abs\_m}$ is used as a feature-data parameter x to determine whether the target concavity is a lesion or a non-lesion, the following process is performed in advance. Sample regions that represent various medical conditions, such as bleeding, are collected as teacher data. The sample regions are categorized into some lesion groups on the medical-condition basis. A pixel-value average $\mu_k$ and a pixel-value covariance $\Sigma_k$ of each of the lesion groups are calculated, in which k indicates the group number of the lesion group. Samples are collected even from the concavities that are not the suspected lesion regions. These samples are categorized into non-lesion groups in such a manner that some having the same factor because of which they are extracted as the concavities or some having the pixel-value averages closer to each other are categorized to the same non-lesion group. A pixel-value average $\mu_i$ and a pixel-value covariance $\Sigma_i$ of each of the non-lesion groups are calculated, in which i indicates the group number of the non-lesion group.

A probability that the target concavity to be compared is generated from a distribution of a lesion group is calculated using the following equation (18) where the distribution of each of the lesion groups is assumed to be a normal distribution, and a probability that the target concavity is generated from a distribution of a non-lesion group is calculated using the following equation (19) where the distribution of each of the non-lesion groups is assumed to be a normal distribution:

$$p(k|x) = \frac{1}{(2\pi)^{n/2}|\Sigma_k|^{1/2}} \exp\left\{-\frac{1}{2}(x-\mu_k)^t(\Sigma_k)^{-1}(x-\mu_k)\right\} \quad (18)$$

$$p(i|x) = \frac{1}{(2\pi)^{n/2}|E_i|^{1/2}} \exp\left\{-\frac{1}{2}(x-\mu_i)^t(\Sigma_i)^{-1}(x-\mu_i)\right\} \quad (19)$$

where n in equations (18) and (19) is the dimension number of the feature data. If the average of pixel values within the region ($R_{abs\_m}$, $G_{abs\_m}$, $B_{abs\_m}$) is used as the feature-data parameter x, n=3.

A probability $p_{k=a}$ that the target concavity belongs to a certain medical condition a is then calculated using the following equation (20) using the probability p(k|x), which is calculated using equation (18) as the probability that the target concavity is generated from a distribution of a lesion group, and the probability p(i|x), which is calculated using equation (19) as the probability that the target concavity is generated from a distribution of a non-lesion group:

$$p_{k=a} = \frac{p(k=a|x)}{\sum p(i|x) - \sum p(k|x)} \quad (20)$$

In equation (20), the probability that the target concavity having the feature-data parameter x is generated from the distribution of the lesion group that represents the medical condition a is expressed by p(k=a|x). The sum of the probabilities that the target concavity is generated from a distribution of a non-lesion group is expressed by $\Sigma p(i|x)$. The sum of the probabilities that the target concavity is generated from a distribution of a lesion group is expressed by $\Sigma p(k|x)$. In this manner, the probability $p_{k=a}$ that the target concavity belongs to the certain medical condition a is calculated by normalizing the target concavity having the certain feature-data parameter x using the sum of the probabilities of all the groups that the target concavity is generated from a lesion group.

The probability that the target concavity belongs to a certain medical condition is calculated on each medical condition using equation (20). The value of the medical condition having the highest probability among the calculated probabilities is assumed to be $p(k=a_{max}|x)$. If this value is equal to or lower than a predetermined threshold LesionProbTh, i.e., $p(k=a_{max}|x) \leq$ LesionProbTh, the target concavity is determined to be a concavity that is generated due to a factor other than a lesion and excluded from the concavities that are possibly the suspected lesion region. The remaining concavities are extracted as the suspected concavity lesion regions.

Subsequently, the regional-feature-data determining unit 16c performs the processing on the convexities that are possibly the suspected lesion regions in the same manner as it determines at Step S205 whether the concavity is a lesion or a non-lesion and excludes the convexity having the feature data that indicates something other than lesions, thereby refining the suspected lesion regions (Step S206). After that, the process control returns to Step S2 of FIG. 2. That is, it calculates the probability, which is generated from a distribution of a group of the prepared teacher data, and determines whether the target region is a lesion or a non-lesion. Then, the convexities that are generated due to a factor other than a lesion are excluded from the convexities that are possibly the suspected lesion regions. The remaining convexities are extracted as the suspected convexity lesion regions.

The feature-data parameter that is used to determine whether the target region is the region that is possibly the suspected lesion region is not limited to the average of pixel values within the region ($R_{abs\_m}$, $G_{abs\_m}$, $B_{abs\_m}$). Some other values, such as the area of the region $S_{\_m}$, the perimeter of the region $L_{\_m}$, the Feret's diameter of the region $Fere_{\_m}(\theta)$, the longer diameter of the region $L_{l\_m}$, the shorter diameter of the region $L_{s\_m}$, the ratio between the longer diameter and the shorter diameter $L_{r\_m}$, the edge strength of the outline of region $E_{\_m}$, and the degree of circularity of the region $C_{\_m}$ can be used. Moreover, it is allowable to combine these values appropriately. The process at Step S206 using the convexities can be performed prior to the process at Step S205 using the concavities, or these processes can be performed in parallel.

Figure 8:
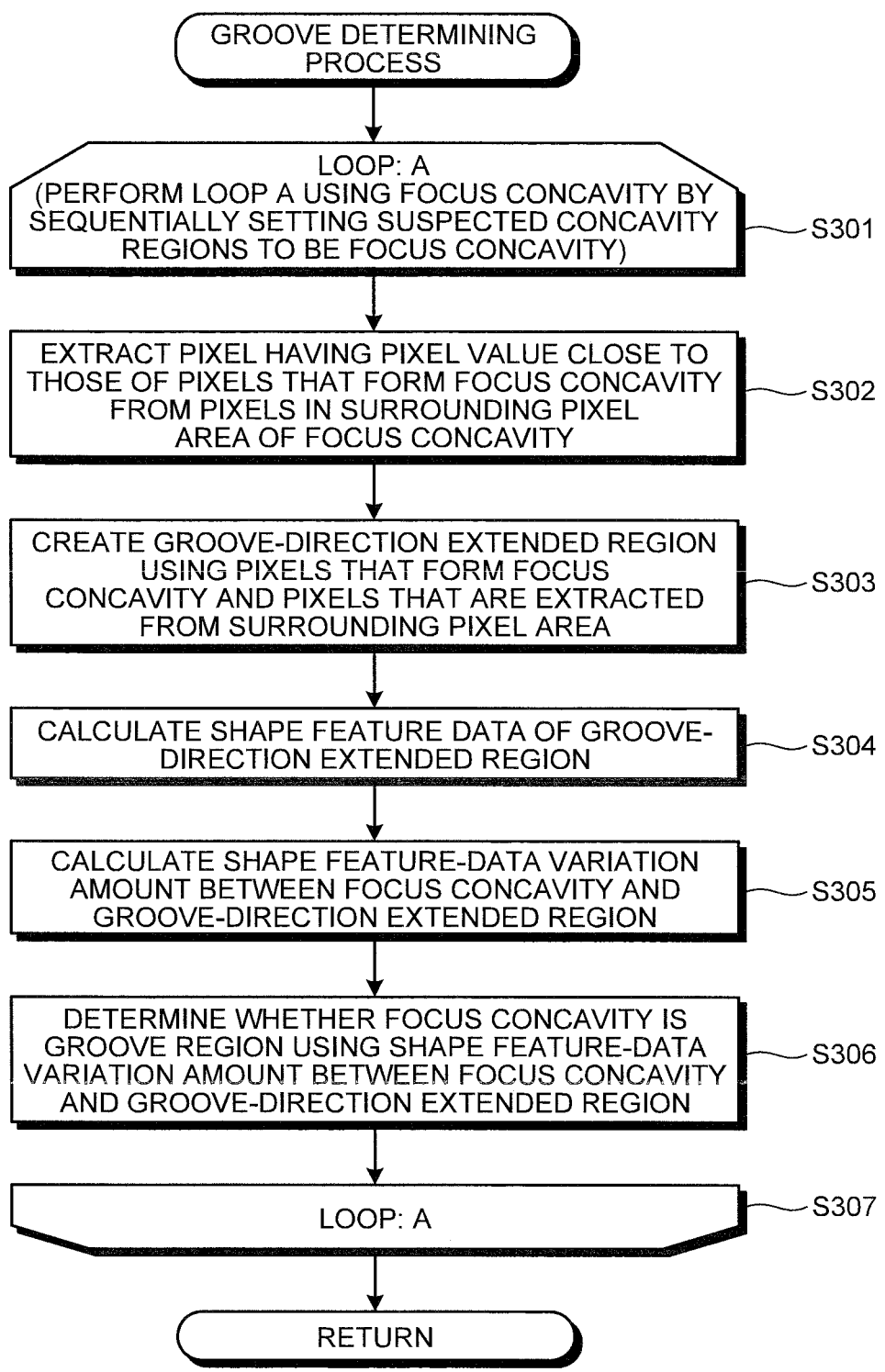
FIG. 8 is a flowchart showing a groove determining process in detail.

The groove determining process at Step S3 of FIG. 2 is described below. FIG. 8 is a flowchart showing the groove determining process in detail. In the groove determining process, each of the suspected concavity lesion regions is subjected to a set of processes indicated by a loop A (Steps S301 to S307). The reason why the suspected concavity lesion regions are in focus is that a part corresponding to a groove that is formed between in-vivo organ walls is included in regions that are depressing more than the surroundings. In the explanation about the processes of the loop A, the suspected concavity lesion region to be processed is referred to as a focus concavity.

In the loop A, the surrounding-similar-pixel extracting unit 17a first extracts a pixel having a pixel value that is close to those of the pixels that form the focus concavity from pixels surrounding the focus concavity (Step S302). Specifically, the surrounding-similar-pixel extracting unit 17a first defines a surrounding pixel area that is a predetermined area surrounding the focus concavity.

Figures 1, 9:
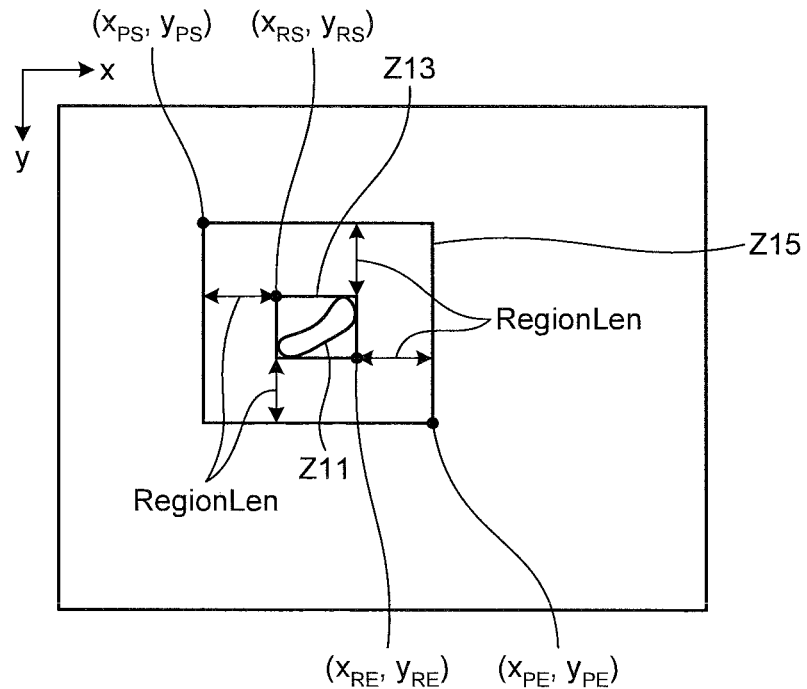
Figures 2, 9:
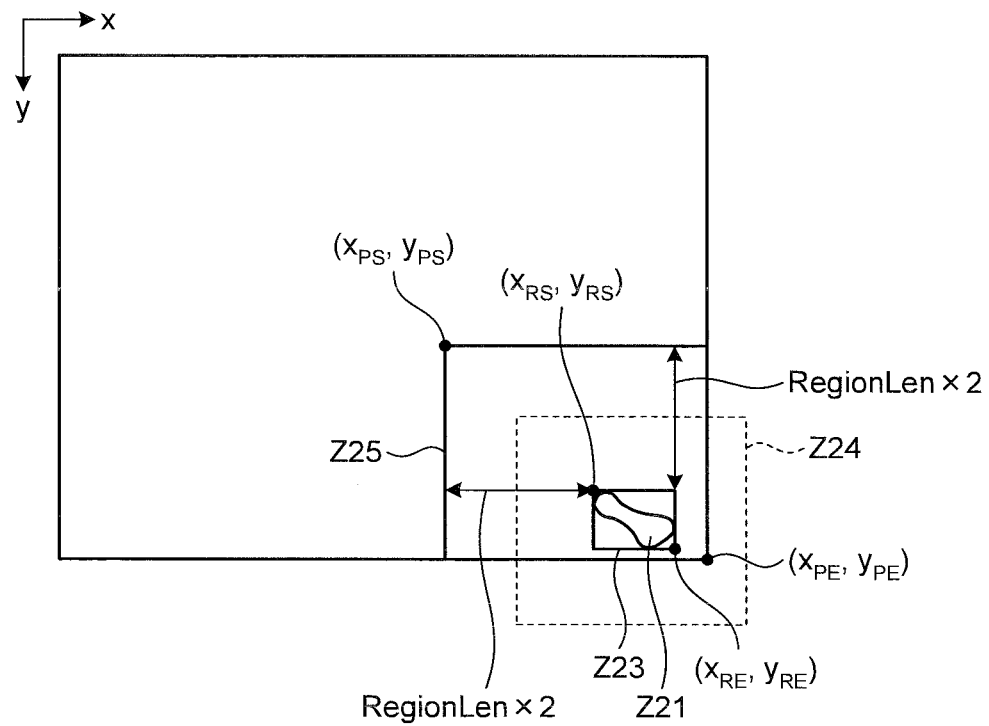

FIGS. 9-1 and 9-2 are schematic diagrams that explain how to define the surrounding pixel area. The surrounding pixel area is defined by calculating, using a start coordinate point ($x_{RS}$, $y_{RS}$) and an end coordinate point ($x_{RE}$, $y_{RE}$) of a bounding rectangle Z13 of a focus concavity Z11, a start coordinate point ($x_{PS}$, $y_{PS}$) and an end coordinate point ($x_{PE}$, $y_{PE}$) of a rectangular region Z15 that is obtained by extending the bounding rectangle Z13 using an extension value RegionLen. In the present embodiment, the extension value RegionLen depends on a size of the focus concavity as is clear from, for example, the following equation (21). As shown in FIG. 9-2, if a focus concavity Z21 is positioned near a corner of the image, specifically, if an area Z24 that is outside the image area as indicated by dot lines shown in FIG. 9-2 is obtained when the surrounding pixel area is defined using the method that is described with reference to FIG. 9-1, the surrounding pixel area is defined in the following manner. The extension value RegionLen that is a value by which the region is extended in a direction opposite to a direction in which it is outside the image area is set, for example, double. In the example shown in FIG. 9-2, the area Z24 indicated by the dotted lines is outside the side of the image area running toward right in FIG. 9-2 along the x axis and the side of the image area running toward the bottom in FIG. 9-2 along the y axis. The surrounding pixel area is defined by calculating the start coordinate point ($x_{PS}$, $y_{PS}$) and the end coordinate point ($x_{PE}$, $y_{PE}$) of the rectangular region Z25 that is obtained by extending by RegionLen×2 in both the leftward direction in FIG. 9-2 along the negative x axis and the upward direction in FIG. 9-2 along the negative y axis. With this configuration, even if the focus concavity is present near an edge of the image, it is possible to define the large-enough surrounding pixel area. Therefore, a pixel having a pixel value close to those of the pixels that form the focus concavity can be extracted with a high accuracy in the later-described process.

Actually, the surrounding pixel area is calculated and defined using the following equations (21) to (25) using the start coordinate point ($x_{RS}$, $y_{RS}$) and the end coordinate point ($x_{RE}$, $y_{RE}$) of the bounding rectangle of the focus concavity. ImgSizeX is a size of the in-vivo image in the x coordinate. ImgSizeY is a size of the in-vivo image in the y coordinate.

$$RegionLen = \sqrt{(x_{RE} - x_{RS})^2 + (y_{RE} - y_{RS})^2} \quad (21)$$

$$x_{PS} = \begin{cases} x_{RS} - RegionLen & (22) \\ \begin{pmatrix} \text{IF } x_{PE} < ImgSizeX \text{ is} \\ \text{calculated using Equation (24)} \end{pmatrix} \\ x_{RS} - RegionLen \times 2 \\ \begin{pmatrix} \text{IF } x_{PE} \geq ImgSizeX \text{ is} \\ \text{calculated using Equation (24)} \end{pmatrix} \end{cases}$$

If $x_{PS} < 0$, $x_{PS}$ is set to 0 after evaluated using Equation (24).

$$y_{PS} = \begin{cases} y_{RS} - RegionLen & (23) \\ \begin{pmatrix} \text{IF } y_{PE} < ImgSizeY \text{ is} \\ \text{calculated using Equation (25)} \end{pmatrix} \\ y_{RS} - RegionLen \times 2 \\ \begin{pmatrix} \text{IF } y_{PE} \geq ImgSizeY \text{ is} \\ \text{calculated using Equation (25)} \end{pmatrix} \end{cases}$$

If $y_{PS} < 0$, $y_{PS}$ is set to 0 after evaluated using Equation (25).

$$x_{PE} = \begin{cases} x_{RE} + RegionLen & (24) \\ \begin{pmatrix} \text{IF } x_{PS} \geq 0 \text{ is calculated} \\ \text{using Equation (22)} \end{pmatrix} \\ x_{RE} + RegionLen \times 2 \\ \begin{pmatrix} \text{IF } x_{PS} < 0 \text{ is calculated} \\ \text{using Equation (22)} \end{pmatrix} \end{cases}$$

If $x_{PE} \geq ImgSizeX$,
$x_{PE}$ is set to ImgSizeX−1 after evaluated using Equation (22).

$$y_{PE} = \begin{cases} y_{RE} + RegionLen & (25) \\ \begin{pmatrix} \text{IF } y_{PS} \geq 0 \text{ is calculated} \\ \text{using Equation (23)} \end{pmatrix} \\ y_{RE} + RegionLen \times 2 \\ \begin{pmatrix} \text{IF } y_{PS} < 0 \text{ is calculated} \\ \text{using Equation (23)} \end{pmatrix} \end{cases}$$

If $Y_{PE} \geq ImgSizeY$,
$Y_{PE}$ is set to ImgSizeY−1 after evaluated using Equation (23).

The method of setting the surrounding pixel area is not limited to the setting method using the start point ($x_{RS}$, $y_{RS}$) and the end coordinate point ($x_{RE}$, $y_{RE}$) of the bounding rectangle of the focus concavity. Some other values, such as a length of the diagonal of the bounding rectangle of the focus concavity, the area, the Feret's diameter, the longer diameter, and the shorter diameter of the focus concavity, can be used.

The surrounding-similar-pixel extracting unit 17a then extracts a pixel having a pixel value close to those of the pixels that form the focus concavity from the pixels $I_p$ (x, y, z) (x=$x_{PS}$, ..., $x_{PE}$, y=$y_{PS}$, ..., $y_{PE}$, z=R, G, B). Because the area from which pixels are extracted is limited to the surrounding pixel area, it is possible to reduce the calculation load and improve the processing speed. Specifically, if the pixel $I_P$ satisfies the following inequalities (26) to (28), the pixel $I_P$ is extracted as the pixel having the pixel value close to those of the pixels that form the focus concavity. This determination is made using at least one of the brightness, the chromaticity, and the color difference of the pixel containing the G component. In most true lesion regions where bleeding or discoloration of organ tissues is observed, an abnormality appears in the blood flowing through organ tissues. Therefore, the G component, which is corresponding to the blood bleeding band and is sensible enough to show a difference between the healthy region and the lesion region in the form of the pixel value, is used. SimilarGValTh, SimilarG_RValTh, and SimilarGBValTh are predetermined thresholds. $R_{abs\_m}$ is an average of the R components within the region of the focus concavity; $G_{abs\_m}$ is the G components within the region of the focus concavity; and $B_{abs\_m}$ is the B components within the region of the focus concavity.

$$|I_p(x, y, G) - G_{abs\_m}| \leq SimilarGValTH \quad (26)$$

$$\left| \frac{I_p(x, y, G)}{I_p(x, y, R)} - \frac{G_{abs\_m}}{R_{abs\_m}} \right| \leq SimilarG\_RValTH \quad (27)$$

$$\left| \begin{array}{c} (I_p(x, y, G) - I_p(x, y, B)) - \\ (G_{abs\_m} - B_{abs\_m}) \end{array} \right| \leq SimilarGBValTH \quad (28)$$

Subsequently, the extended-groove-region creating unit 17b creates a groove-direction extended region (Step S303) and calculates shape feature data of the created groove-direction extended region (Step S304). Specifically, the extended-groove-region creating unit 17b performs well-know region definition process using particle analysis by using both the pixels that contribute the focus concavity and the pixels that are extracted from the surrounding pixel area at Step S302 because they have pixel values close to those of the focus concavity and sets the obtained region to be the groove-direction extended region. The extended-groove-region creating unit 17b calculates the shape feature data of the groove-direction extended region using the particle analysis. The extended-groove-region creating unit 17b calculates, for example, an area ES_$m$ of the obtained groove-direction extended region as the shape feature data.

After that, the extended-groove-region creating unit 17b calculates a ratio RS_$m$ between the area S_$m$ of the focus concavity and the area ES_$m$ of the groove-direction extended region using the following equation (29) as a shape feature-data variation amount between the focus concavity and the groove-direction extended region that is created based on the focus concavity (Step S305).

$$RS\_m = \frac{ES\_m}{S\_m} \quad (29)$$

The shape feature data that is calculated at Step S304 is not limited to the area of the groove-direction extended region. Some other values, such as the perimeter of the region, the Feret's diameter, the longer diameter of the region, the shorter diameter of the region, the ratio between the longer diameter and the shorter diameter, can be calculated. The shape feature-data variation amount that is calculated at Step S305 is not limited to the ratio between the area of the focus concavity and the area of the groove-direction extended region. Some other values, such as the difference in the perimeter of the region, the difference in the Feret's diameter of the region, the difference between the longer diameter and the shorter diameter of the region, and the difference in the ratio between the longer diameter and the shorter diameter of the region, can be calculated in accordance with the shape feature data.

If the ratio $RS\_m$ between the area $S\_m$ of the region and the area $ES\_m$ of the groove-direction extended region satisfies the following inequality (30), the extended-groove-region creating unit 17b determines that the focus concavity is the groove region (Step S306):

$$RS\_m > \text{SurroundAreaDifTh} \qquad (30)$$

where SurroundAreaDifTh is a predetermined threshold.

After each of the suspected lesion regions has been subjected to the processes of the loop A as the focus concavity, the process control returns to Step S3 of FIG. 2.

The lesion-region extracting process at Step S4 of FIG. 2 is described below. In the lesion-region extracting process, the lesion-region extracting unit 18 excludes the suspected concavity lesion region that is determined to be the groove region in the groove determining process from the suspected lesion regions and extracts the remaining suspected concavity regions and the suspected convexity regions that are extracted at Step S206 as the lesion regions.

Figure 10:
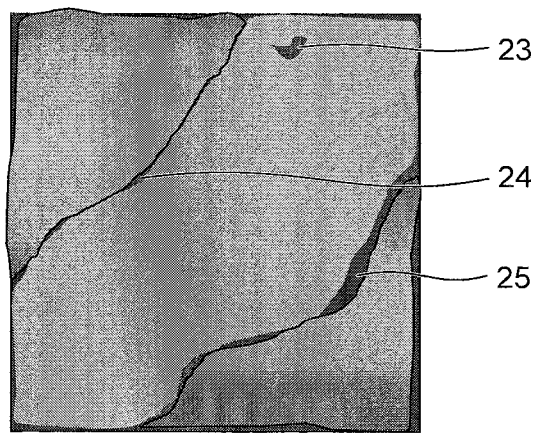
FIG. 10 is a display example of an in-vivo image.
Figure 11:
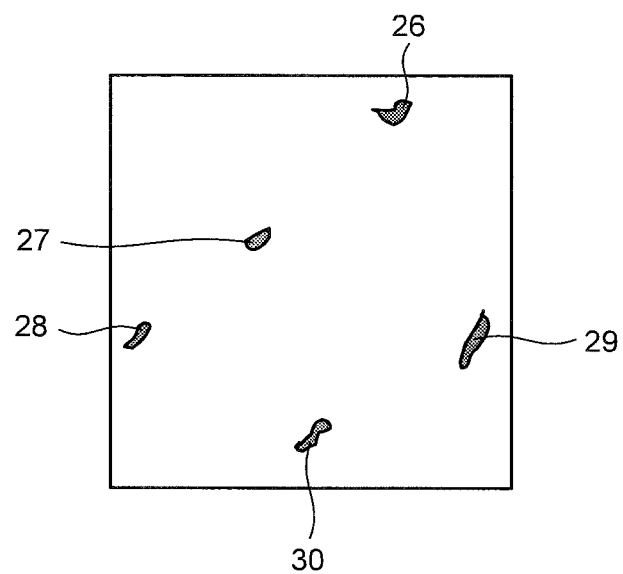
FIG. 11 is an example of an extracted concavity image that represents a suspected concavity region that is extracted from the in-vivo image shown in FIG. 10.

An example of the lesion region extracted in the present embodiment from an exemplary in-vivo image is described below. FIG. 10 is a display example of an original in-vivo image. The in-vivo image shown in FIG. 10 includes a bleeding section 23 and grooves 24 and 25 that are formed between organ walls. FIG. 11 is an example of an extracted concavity image that represents the suspected concavity region that is extracted from the in-vivo image shown in FIG. 10. In the example shown in FIG. 11, a plurality of suspected concavity lesion regions 26 to 30 having the substantially same area that is extracted through the suspected-lesion-region extracting process is shown.

Figure 12:
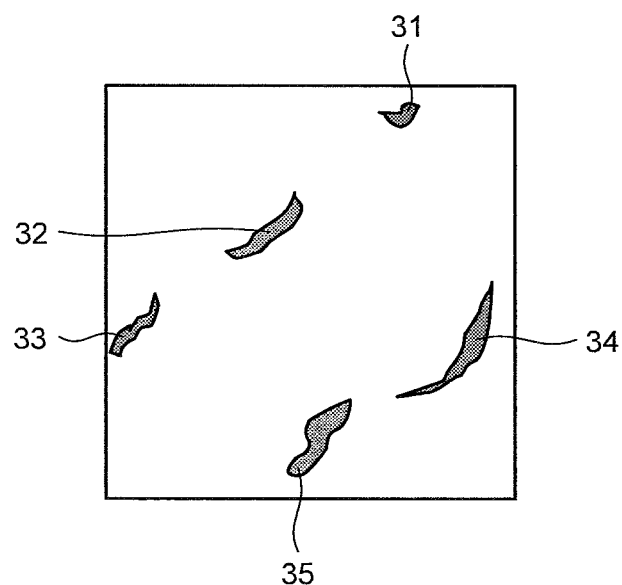
FIG. 12 is an example of a groove-direction extended region that is created from the suspected concavity lesion region shown in the extracted concavity image of FIG. 11.

FIG. 12 is an example of the groove-direction extended region that is created from each of the suspected concavity lesion regions 26 to 30 shown in the extracted concavity image of FIG. 11. As shown in FIG. 12, the suspected concavity lesion regions 27 and 28 (see FIG. 11), which are associated with the groove 24 that is formed between the organ walls (see FIG. 10), are extended in the direction in which the pixels that form the groove 24 are arranged and converted to groove-direction extended regions 32 and 33, respectively. The suspected concavity lesion regions 29 and 30 (see FIG. 11), which are associated with the groove 25 that is formed between the organ walls (see FIG. 10) are extended in the direction in which the pixels that form the groove 25 are arranged and converted to groove-direction extended regions 34 and 35, respectively. In the suspected concavity lesion region that is associated with the groove, because the pixel value, such as brightness, changes gradually as it goes along the groove, pixels having pixels values close to each other are arranged along the groove direction. Therefore, the created groove-direction extended region is extended in the groove direction from the original extracted concavity image.

The suspected concavity lesion region 26 that is associated with the bleeding section 23 is converted to a groove-direction extended region 31 shown in FIG. 12 as a result of creation of the groove-direction extended region. A change from the suspected concavity lesion region 26 to the groove-direction extended region 31 is not large. In most lesion regions, such as a bleeding section, the pixel value, such as the brightness, the color ratio, and the color difference, changes drastically when it comes from the surrounding area to the lesion region. The probability that a pixel having a close pixel value is present in the surrounding area is low. Therefore, a change from the original extracted concavity image to the created groove-direction extended region is small.

In this manner, the lesion-region extracting unit 18 determines, while assuming that the suspected concavity lesion regions 27, 28, 29, and 30 shown in FIG. 11 that are extended by the process performed by the groove determining unit 17 in the direction in which the pixels that form the groove to be the groove regions, the suspected concavity lesion region 26, which is not extended largely, to be the lesion region and finally extracts the suspected concavity lesion region 26 as the lesion region.

Figure 13:
FIG. 13 is a display example of the extracted lesion region.

After the lesion region is extracted, a lesion region 36 is displayed as an extracted lesion image in a recognizable manner on the display unit 15 at Step S5 of FIG. 2 as shown in FIG. 13, for example. The display manner is not limited to the manner shown in FIG. 13 in which the extracted lesion region in a color different from a color of the background is displayed on a background image (in, for example, black color) having the same size as the original in-vivo image. For example, it is allowable to display this extracted lesion image overlapped with the in-vivo image. Alternatively, it is allowable to display the outline of the lesion region on the in-vivo image so that the lesion region within the in-vivo image can be identified.

According to the present embodiment, the accuracy in detecting a lesion region is maintained high, regardless of change of the pixel value due to, for example, how grooves and part other than the grooves are exposed to an illumination light. Therefore, an image processing apparatus that is stable against difference in an in-vivo image taking environment can detect the lesion region with a high accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a suspected-lesion-region extracting unit that extracts a suspected lesion region by determining that a region is concave from an in-vivo image that is obtained by taking an image of inside of a body of an inspection subject using illumination light;
   wherein the illumination light inside the body illuminates the suspected lesion region inside the body of the patient;
   a groove determining unit that determines whether the suspected lesion region is a region corresponding to a shadow of a groove that is formed between in-vivo organ walls; and
   a lesion-region extracting unit that extracts a lesion region using the suspected lesion region and a result of determination by the groove determining unit, wherein the groove determining unit includes:
   a surrounding-similar-pixel extracting unit that determines whether pixels from pixels surrounding the suspected lesion region in the in-vivo image have a pixel value similar to the pixel values of pixels that form the suspected lesion region; and
   an extended-groove-region creating unit that
   creates, in the in-vivo image, a groove-direction extended region formed of the pixels that form the extracted suspected lesion region and the pixels determined by the surrounding-similar-pixel extracting unit and
   determines, using the extracted suspected lesion region and the created groove-direction extended region, whether the extracted suspected lesion region is the region corresponding to the shadow of the groove that is formed between in-vivo organ walls,
wherein the extended-groove-region creating unit determines whether the suspected lesion region in the in-vivo image is a region corresponding to the shadow of the groove that is formed between in-vivo organ walls using a calculated amount between the extracted suspected lesion region and the created groove-direction extended region, the calculated amount representing an amount of variation between a shape in the suspected lesion region and a shape in the groove-direction extended region.

2. The image processing apparatus according to claim 1, wherein the surrounding-similar-pixel extracting unit sets a predetermined area surrounding the suspected lesion region to be a surrounding pixel area and extracts, from the surrounding pixel area, a pixel having a pixel value close to those of the pixels that form the suspected lesion region.

3. The image processing apparatus according to claim 2, wherein the surrounding-similar-pixel extracting unit calculates the surrounding pixel area using shape feature data of the suspected lesion region.

4. The image processing apparatus according to claim 3, wherein the surrounding-similar-pixel extracting unit calculates the surrounding pixel area using at least one of coordinates of a bounding rectangle of the suspected lesion region, a length of a diagonal of the bounding rectangle, an area of the suspected lesion region, a Feret's diameter of the suspected lesion region, a longer diameter of the suspected lesion region, and a shorter diameter of the suspected lesion region.

5. The image processing apparatus according to claim 3, wherein the surrounding-similar-pixel extracting unit calculates the surrounding pixel area by extending a bounding rectangle of the suspected lesion region by a predetermined value using coordinates of the bounding rectangle, wherein, if the calculated surrounding pixel area is outside an image area of the in-vivo image, the surrounding-similar-pixel extracting unit calculates the surrounding pixel area by extending, by a value larger than the predetermined value, the bounding rectangle in a direction opposite to a direction in which the calculated surrounding pixel area is outside the image area.

6. The image processing apparatus according to claim 2, wherein the surrounding-similar-pixel extracting unit extracts a pixel, from the surrounding pixel area, that is similar in terms of at least one of brightness, color ratio, and color difference to the pixels that form the suspected lesion region.

7. The image processing apparatus according to claim 6, wherein the surrounding-similar-pixel extracting unit uses a color component corresponding to a blood absorbing band to measure at least one of the brightness, the color ratio, and the color difference of the pixels that form the suspected lesion region and the pixel in the surrounding pixel area.

8. The image processing apparatus according to claim 7, wherein the color component corresponding to the blood absorbing band is a G component.

9. The image processing apparatus according to claim 1, wherein the calculated amount is at least one of a ratio between an area of the groove-direction extended region and an area of the suspected lesion region, a difference between a perimeter of the groove-direction extended region and a perimeter of the suspected lesion region, a difference between a Feret's diameter of the groove-direction extended region and a Feret's diameter of the suspected lesion region, and a difference between a ratio between a longer diameter and a shorter diameter of the groove-direction extended region and a ratio between a longer diameter and a shorter diameter of the suspected lesion region.

10. The image processing apparatus according to claim 1, wherein the groove determining unit determines whether a region that is depressing more than a surrounding in-vivo organ wall and is selected from the suspected lesion regions is a region corresponding to a shadow of a groove that is formed between in-vivo organ walls.

11. The image processing apparatus according to claim 1, wherein the lesion-region extracting unit extracts, as the lesion region, a region that is obtained by excluding from the suspected lesion regions the region that is determined by the groove determining unit to be a region corresponding to a shadow of a groove that is formed between in-vivo organ walls.

12. The image processing apparatus according to claim 1, wherein the suspected-lesion-region extracting unit includes
a different-pixel extracting unit that sets pixels of the in-vivo image to be a focus pixel sequentially, calculates a pixel-value variation amount between the focus pixel and a pixel surrounding the focus pixel, and extracts pixels associated with the suspected lesion using the pixel-value variation amount from the focus pixels;
a region-data obtaining unit that extracts a region that is possibly the suspected lesion region using the pixels associated with the suspected lesion region and calculates feature data on the region; and
a regional-feature-data determining unit that determines using the feature data whether the region that is possibly the suspected lesion region is the suspected lesion region.

13. The image processing apparatus according to claim 12, wherein the different-pixel extracting unit extracts, using the pixel-value variation amount between the focus pixel and the pixel surrounding the focus pixel, pixels of a region that is protruding or depressing more than a surrounding in-vivo organ wall as the pixels associated with the suspected lesion region.

14. The image processing apparatus according to claim 12, wherein the different-pixel extracting unit uses a color component corresponding to a blood absorbing band to calculate the pixel-value variation amount.

15. The image processing apparatus according to claim 14, wherein the color component corresponding to the blood absorbing band is a G component.

16. The image processing apparatus according to claim 12, wherein, if a region is the suspected lesion region, the region-data obtaining unit calculates as the feature data at least one of an average of pixel values within the region, an average of pixel-value variation amounts within the region, an area of the region, a perimeter of the region, a Feret's diameter of the region, a longer diameter of the region, a shorter diameter of the region, a ratio between the longer diameter and the shorter diameter, an edge strength of an outline of the region, and a degree of circularity of the region.

17. The image processing apparatus according to claim 1, wherein an area between outer border of the extracted suspected lesion region and outer border of the groove-direction extended region comprises pixels having pixel values similar to the pixel values of the suspected lesion region.

18. A non-transitory computer-readable recording medium recording therein a program that, when executed by a computer, causes the computer to perform:
a suspected-lesion-region extracting that extracts a suspected lesion region by determining that a region in concave from an in-vivo image that is obtained by taking an image of inside of a body of an inspection subject using illumination light;

wherein the illumination light inside the body illuminates the suspected lesion region inside the body of the patient;

a groove determining that determines whether the suspected lesion region is a region corresponding to a shadow of a groove that is formed between in-vivo organ walls; and a lesion-region extracting that extracts a lesion region using the suspected lesion region and a result of determination by the groove determining, wherein the groove determining includes:

determining whether pixels from pixels surrounding the suspected lesion region in the in-vivo image have a pixel value similar to pixel values of pixels that form the suspected lesion region; and creating, in the in-vivo image, a groove-direction extended region formed of the pixels that form the extracted suspected lesion region and the pixels determined to have a pixel value similar to pixel values of pixels that form the suspected lesion region and determines, using the extracted suspected lesion region and the created groove-direction extended region, whether the extracted suspected lesion region is the region corresponding to the shadow of the groove that is formed between in-vivo organ walls, wherein the creating the groove-extended region determines whether the suspected lesion region in the in-vivo image is a region corresponding to the shadow of the groove that is formed between in-vivo organ walls using a calculated amount between the extracted suspected lesion region and the created groove-direction extended region, the calculated amount representing an amount of variation between a shape in the suspected lesion region and a shape in the groove-direction extended region.

19. An image processing method comprising:

a suspected-lesion-region extracting that extracts a suspected lesion region by determining that a region is concave from an in-vivo image that is obtained by taking an image of inside of a body of an inspection subject using illumination light;

wherein the illumination light inside the body illuminates the suspected lesion region inside the body of the patient;

a groove determining that determines whether the suspected lesion region is a region corresponding to a shadow of a groove that is formed between in-vivo organ walls; and a lesion-region extracting that extracts a lesion region using the suspected lesion region and a result of determination by the groove determining, wherein the groove determining includes:

determining whether pixels from pixels surrounding the suspected lesion region in the in-vivo image have a pixel value similar to pixel values of pixels that form the suspected lesion region; and creating, in the in-vivo image, a groove-direction extended region formed of the pixels that form the extracted suspected lesion region and the pixels determined to have a pixel value similar to pixel values of pixels that form the suspected lesion region and determines, using the extracted suspected lesion region and the created groove-direction extended region, whether the extracted suspected lesion region is the region corresponding to the shadow of the groove that is formed between in-vivo organ walls, wherein the creating the extended-groove-region determines whether the suspected lesion region in the in-vivo image is a region corresponding to the shadow of the groove that is formed between in-vivo organ walls using a calculated amount between the extracted suspected lesion region and the created groove-direction extended region, the calculated amount representing an amount of variation between a shape in the suspected lesion region and a shape in the groove-direction extended region.

20. The image processing method according to claim 19, wherein the surrounding-similar-pixel extracting sets a predetermined area surrounding the suspected lesion region to be a surrounding pixel area and extracts, from the surrounding pixel area, a pixel having a pixel value close to those of the pixels that form the suspected lesion region.

21. The image processing method according to claim 20, wherein the surrounding-similar-pixel extracting calculates the surrounding pixel area using shape feature data of the suspected lesion region.

22. The image processing method according to claim 21, wherein the surrounding-similar-pixel extracting calculates the surrounding pixel area using at least one of coordinates of a bounding rectangle of the suspected lesion region, a length of a diagonal of the bounding rectangle, an area of the suspected lesion region, a Feret's diameter of the suspected lesion region, a longer diameter of the suspected lesion region, and a shorter diameter of the suspected lesion region.

23. The image processing method according to claim 21, wherein the surrounding-similar-pixel extracting calculates the surrounding pixel area by extending a bounding rectangle of the suspected lesion region by a predetermined value using coordinates of the bounding rectangle, wherein, if the calculated surrounding pixel area is outside an image area of the in-vivo image, the surrounding-similar-pixel extracting calculates the surrounding pixel area by extending, by a value larger than the predetermined value, the bounding rectangle in a direction opposite to a direction in which the calculated surrounding pixel area is outside the image area.

24. The image processing method according to claim 20, wherein the surrounding-similar-pixel extracting extracts a pixel, from the surrounding pixel area, that is similar in terms of at least one of brightness, color ratio, and color difference to the pixels that form the suspected lesion region.

25. The image processing method according to claim 24, wherein the surrounding-similar-pixel extracting uses a color component corresponding to a blood absorbing band to measure at least one of the brightness, the color ratio, and the color difference of the pixels that form the suspected lesion region and the pixel in the surrounding pixel area.

26. The image processing method according to claim 25, wherein the color component corresponding to the blood absorbing band is a G component.

27. The image processing method according to claim 19, wherein the calculated amount is at least one of a ratio between an area of the groove-direction extended region and an area of the suspected lesion region, a difference between a perimeter of the groove-direction extended region and a perimeter of the suspected lesion region, a difference between a Feret's diameter of the groove-direction extended region and a Feret's diameter of the suspected lesion region, and a difference between a ratio between a longer diameter and a shorter diameter of the groove-direction extended region and a ratio between a longer diameter and a shorter diameter of the suspected lesion region.

28. The image processing method according to claim 19, wherein the groove determining includes determining whether a region that is depressing more than a surrounding in-vivo organ wall and is selected from the suspected lesion regions is a region corresponding to a shadow of a groove that is formed between in-vivo organ walls.

29. The image processing method according to claim 19, wherein the lesion-region extracting includes extracting, as the lesion region, a region that is obtained by excluding from the suspected lesion regions the region that is determined at the groove determining to be a region corresponding to a shadow of a groove that is formed between in-vivo organ walls.

30. The image processing method according to claim 19, wherein the suspected-lesion-region extracting includes
   a different-pixel extracting of setting pixels of the in-vivo image to be a focus pixel sequentially, calculating a pixel-value variation amount between the focus pixel and a pixel surrounding the focus pixel, and extracting pixels associated with the suspected lesion using the pixel-value variation amount from the focus pixels;
   a region-data obtaining of extracting a region that is possibly the suspected lesion region using the pixels associated with the suspected lesion region and calculating feature data on the region; and
   a regional-feature-data determining of determining using the feature data whether the region that is possibly the suspected lesion region is the suspected lesion region.

31. The image processing method according to claim 30, wherein the different-pixel extracting includes extracting, using the pixel-value variation amount between the focus pixel and the pixel surrounding the focus pixel, pixels of a region that is protruding or depressing more than a surrounding in-vivo organ wall as the pixels associated with the suspected lesion region.

32. The image processing method according to claim 30, wherein the different-pixel extracting includes using a color component corresponding to a blood absorbing band to calculate the pixel-value variation amount.

33. The image processing method according to claim 32, wherein the color component corresponding to the blood absorbing band is a G component.

34. The image processing method according to claim 30, wherein, the region-data obtaining includes calculating as the feature data at least one of an average of pixel values within the suspected lesion region, an average of pixel-value variation amounts within the suspected lesion region, an area of the suspected lesion region, a perimeter of the suspected lesion region, a Feret's diameter of the suspected lesion region, a longer diameter of the suspected lesion region, a shorter diameter of the suspected lesion region, a ratio between the longer diameter and the shorter diameter, an edge strength of an outline of the suspected lesion region, and a degree of circularity of the suspected lesion region.

35. The image processing method according to claim 19, wherein an area between outer border of the extracted suspected lesion region and outer border of the groove-direction extended region comprises pixels having pixel values similar to the pixel values of the suspected lesion region.

\* \* \* \* \*